United States Patent
Chaffringeon

(12) 
(10) Patent No.: US 6,558,362 B1
(45) Date of Patent: May 6, 2003

(54) DISPOSABLE DEVICE FOR TRANSFERRING AN ACTIVE LIQUID INTO A BODY CAVITY

(75) Inventor: Bernard Chaffringeon, 10 Avenue du Léman, CH 1025 Saint Sulpice (CH)

(73) Assignee: Bernard Chaffringeon, Saint-Sulpice (CH)

( * ) Notice: Subject to any disclaimer, the term of this patent is extended or adjusted under 35 U.S.C. 154(b) by 0 days.

(21) Appl. No.: 09/830,426

(22) PCT Filed: Feb. 2, 2000

(86) PCT No.: PCT/FR00/00245

§ 371 (c)(1),
(2), (4) Date: Jun. 1, 2001

(87) PCT Pub. No.: WO00/45887

PCT Pub. Date: Aug. 10, 2000

(30) Foreign Application Priority Data

Feb. 3, 1999  (FR) .............................................. 99 01419

(51) Int. Cl.[7] .......................... A61M 31/00; A61F 13/20
(52) U.S. Cl. ........................ 604/287; 604/904; 604/288
(58) Field of Search ....................... 604/385.17, 385.18, 604/515, 11–15, 18, 285–288, 904; 602/48; 128/832

(56) References Cited

U.S. PATENT DOCUMENTS

| | | |
|---|---|---|
| 706,778 A | 8/1902 | Pond |
| 812,769 A | 2/1906 | Pond |
| 1,561,020 A * | 11/1925 | Pond .......................... 604/287 |
| 1,575,123 A * | 3/1926 | Martocci-Pisculli ........ 604/286 |
| 1,732,413 A * | 10/1929 | Moteram ..................... 604/287 |
| 1,887,526 A | 11/1932 | Spielberg et al. |
| 2,493,416 A | 1/1950 | Negri |
| 3,512,527 A | 5/1970 | Desoye et al. |
| 3,515,138 A | 6/1970 | Hochstrasser et al. |
| 3,519,364 A | 7/1970 | Truhan |

(List continued on next page.)

FOREIGN PATENT DOCUMENTS

| | | |
|---|---|---|
| DE | A1 36 29 994 | 3/1988 |
| EP | A1 0 079 015 | 5/1983 |
| EP | A1 0 577 891 | 1/1994 |
| FR | 2353640 | 12/1977 |
| WO | WO 80/01353 | 7/1980 |
| WO | WO 83/01741 | 5/1983 |

Primary Examiner—Dennis Ruhl
Assistant Examiner—C. Lynne Anderson
(74) Attorney, Agent, or Firm—Oliff & Berridge, PLC

(57) ABSTRACT

The invention concerns a disposable device (1) for transferring an active liquid into a body cavity (2), having sufficient intrinsic consistency for being inserted by being thrust into said cavity, said device comprising: a central element (3), at the source of at least part of the active liquid, a peripheral element (4) arranged around the central element, comprising a pad (5) arranged to collect and absorb the active liquid delivered into the body cavity, by expanding and thereby being urged to press sealingly against the mucous membrane of the body cavity (2). The central element (3) comprises a substrate relatively solid at room temperature outside the body cavity, and turning relatively liquid inside the body cavity, such that therein, said central element is liquefied at least partly to generate at least part of the active liquid.

72 Claims, 1 Drawing Sheet

U.S. PATENT DOCUMENTS

Figure 1:
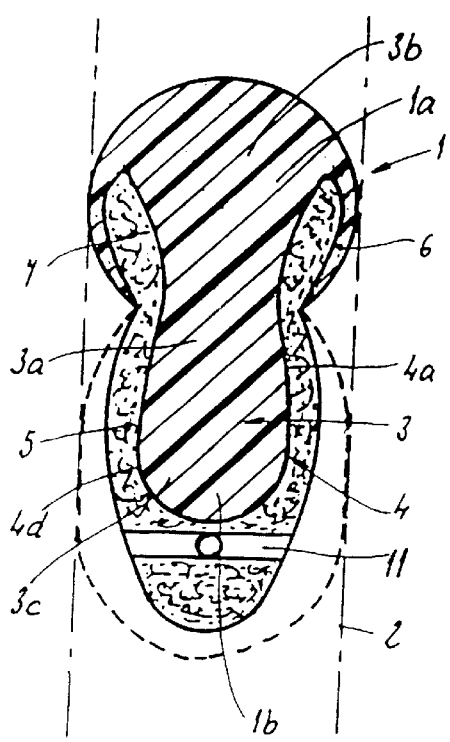

| | | |
|---|---|---|
| 3,521,637 A | 7/1970 | Waterbury |
| 3,559,646 A | 2/1971 | Mullan |
| 3,865,108 A | 2/1975 | Hartop |
| 3,902,493 A * | 9/1975 | Baier et al. .................. 604/286 |
| 3,918,452 A * | 11/1975 | Cornfeld ..................... 424/431 |
| 4,136,680 A | 1/1979 | Southworth |
| 4,232,673 A | 11/1980 | Bucalo |
| 4,257,427 A | 3/1981 | Bucalo |
| 4,286,596 A | 9/1981 | Rubinstein |
| 4,317,454 A | 3/1982 | Bucalo |
| 4,318,405 A | 3/1982 | Sneider |
| 4,324,262 A | 4/1982 | Hall |
| 4,335,720 A | 6/1982 | Glassman |
| 4,582,717 A * | 4/1986 | von Bittera et al. ........ 424/431 |
| 4,858,624 A | 8/1989 | Shihata |
| 5,273,521 A | 12/1993 | Peiler et al. |
| 5,282,789 A | 2/1994 | Lundy |
| 5,299,581 A | 4/1994 | Donnell et al. |
| 5,357,977 A | 10/1994 | Michels |
| 5,542,914 A * | 8/1996 | Van Iten ....................... 604/11 |
| 5,810,745 A | 9/1998 | Chaffringeon |
| 5,823,954 A | 10/1998 | Chaffringeon |
| 5,830,199 A | 11/1998 | Chaffringeon |
| 5,840,055 A | 11/1998 | Sgro |
| 6,059,735 A | 5/2000 | Sgro |

* cited by examiner

DISPOSABLE DEVICE FOR TRANSFERRING AN ACTIVE LIQUID INTO A BODY CAVITY

The present invention relates to the transfer or circulation of an active liquid into or in a body cavity of the human body or of an animal, particularly in contact with the mucous membrane of said cavity.

The term "body cavity" is to be understood as meaning any bodily cavity, particularly an elongate one, which can be accessed externally for various purposes, particularly clinical, therapeutic, prophylactic or diagnostic, but also for cosmetic or personal hygiene purposes. By way of an example of such a cavity, mention may be made of the woman's vagina extending from the vulva to the neck of the uterus, into which an active liquid is to be transferred or in which an active liquid is to be circulated, in contact with the mucous membranes or tissues of said cavity.

In consequence, the term "active liquid" is to be understood as meaning any liquid or fluid for treatment, either locally via a topical route, or systemically and in general comprising a liquid or fluid phase in which a treatment agent is distributed in solution or in suspension. This treatment agent is chosen from the group consisting of wetting agents, agents for solubilizing and fluidizing particularly a bodily fluid or liquid present in the body cavity, therapeutic, prophylactic and diagnostic agents, cosmetic or personal hygiene agents, antiseptics, bactericides, fungicides and spermicides (in the case of the woman's vagina cavity for example).

A subject of the present invention is a disposable device allowing better availability of the active principle or principles in contact with the mucous membrane of the wall of the body cavity, particularly when the treatment agent is therapeutic agent.

Another object of the invention is a device which ensures an almost total absence of external flow of the active liquid and/or of the bodily fluid or of any liquid present in the body cavity in question, throughout the time that said device is present or held in this cavity, simply by constriction thereof.

To this end, according to the invention, the disposable device has sufficient intrinsic consistency that it can be inserted into the body cavity by pushing, and comprises:
  a central element at the source of at least part of the active liquid, in that it comprises a substrate which is relatively solid at ambient temperature and outside the body cavity, and becomes relatively liquid or fluid inside this same cavity and at body temperature so that within this cavity the central element liquefies at least partially to generate at least part of the liquid phase of the active liquid,
  a peripheral element arranged around the central element, in the solid state, comprising a pad designed to collect and absorb the active liquid which has circulated into the body cavity by expanding and thus coming to press in a sealed manner against the mucous membrane of the body cavity.

Figure 2:
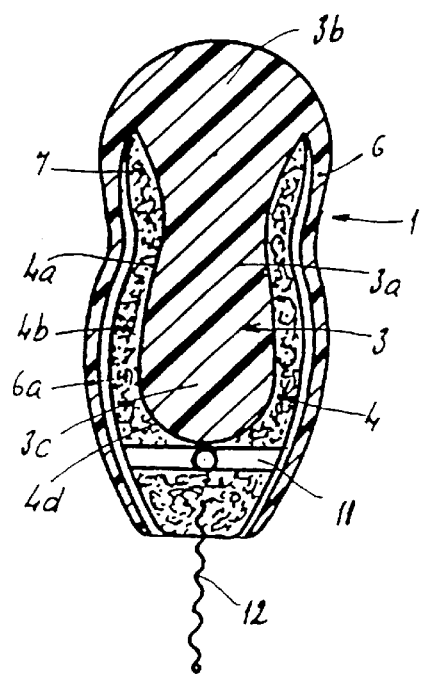
Figure 3:
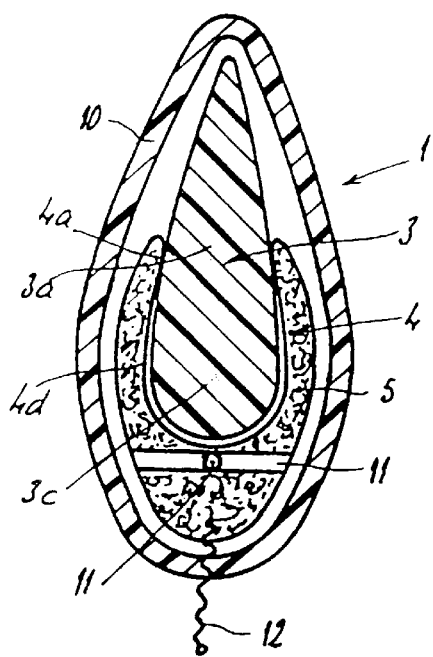
Figure 4:
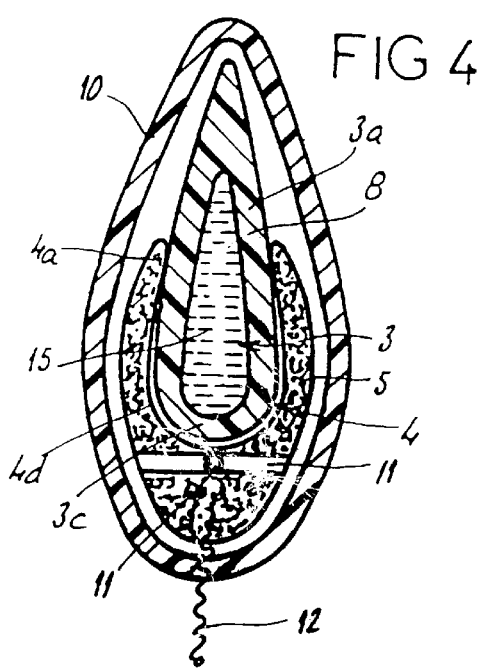

The present invention is now described by way of non-limiting example with reference to the schematic appended drawing in which:

FIG. 1 depicts a disposable device according to the invention, in position in a body cavity, and just after it has been inserted into the latter by pushing, this being according to a first embodiment of the invention; FIG. 1 is an axial section through a device according to the invention, the latter having symmetry of revolution about an axis;

FIGS. 2 to 4 respectively depict three other embodiments of the present invention, still in axial section.

According to FIG. 1, a disposable device according to the invention is referenced by the numerical reference 1. In general, it allows an active liquid as previously defined to be dispensed or released into a body cavity denoted by the numerical reference 2. This device has an intrinsic and overall consistency which is relatively firm but soft and stiff or strong enough to allow it to be inserted into the cavity by pushing, without altering the structure of said device, particularly without dissociating its various components and/or rupturing any liquid-containing capsule that may be contained inside said device (cf. embodiment according to FIG. 4).

The device according to the invention essentially comprises two components assembled together permanently, namely:
  a central element 3 at the source of at least part of the active liquid as previously defined;
  and a peripheral element 4 arranged around the central element 3, comprising a pad 5 designed to absorb the active liquid which has circulated or been dispensed into the body cavity, by expanding and thus coming to press in a relatively sealed manner against the mucous membrane of the body cavity (cf. shape depicted in dotted line in FIG. 1).

The central element 3 comprises a substrate, for example based on gelatin, which is relatively solid at ambient temperature and outside the body cavity and which becomes relatively liquid inside the body cavity and at body temperature so that within this cavity the central element liquefies at least partially to generate at least part of the liquid phase of the active liquid.

The gelatin may be replaced by any other substrate with the same properties, for example a lipid.

In consequence, according to one essential feature of the present invention, it is therefore the substrate of the central element which, by liquefaction within the body cavity, and therefore within the human body or the body of the animal, makes it possible to obtain all or part of the liquid phase of the active liquid.

As a preference, an agent for treating the body cavity as previously described is distributed discretely in the solid substrate of the central element, this being so regardless of the physical form or nature of said treatment agent outside the substrate, for example an oily, solid or liquid physical form, or whether it is hydrophobic or hydrophilic by nature. This discrete distribution of the treatment agent may be achieved by incorporating this agent into the previously defined substrate in the liquid phase when the disposable device according to the invention is being manufactured.

As clearly shown in FIG. 1, the central element 3 is a kind of molded part, molded by the solidification of the liquid substrate, for example the gelatin. And the pad 5 is a sleeve also molded or shaped from a material capable of absorbing a liquid or a fluid as it expands. This material is, for example, a foam of a biocompatible plastic material or alternatively a fibrous material (for example of the cellulose type), opened (for example folded) around the central element 3. The central element 3 and the peripheral element 4 are thus tailored to one another so that they fit together by simple axial pushing of the central element toward the peripheral element or vice versa.

The peripheral element 4 has a hole 4a, or bore, particularly a blind hole as shown in FIG. 1, the shape and size of which are tailored correspondingly to receive the body 3a of the central element 3. The head 3b of the central element 3, of convex external shape, for example spherical, has a collar 6 while the peripheral element 4 has a neck 7, the shape and size of which are tailored to definitively retain the collar 6, by axially pushing the central element 3 and peripheral element 4 together. As shown in FIG. 1, the neck 7 has an undercut accommodating the collar 6 directed inward, and also of convex external shape, for example spherical. The foot 3c of the central element 3 has a bulging shape, while the peripheral element 4 has a correspondingly flared part 4d, the shape and size of which are tailored to retain the foot 3c of the central element 3.

The absorbent material of the pad 5 can expand and/or is spongy and consists, for example, of filaments, capillary fibers, or natural fibers (cellulose or viscose for example), etc. As mentioned earlier, it is the liquefaction or melting of the substrate of the central element 3 which, generating at least part of the liquid phase of the active liquid within the body cavity 2, then allows the pad 5 to expand by collecting said liquid therein, this being the case at body temperature and inside the body cavity 2.

In order possibly to recycle the active liquid in contact with the body cavity 2, the pad 5 is bored for example with four radial passages 11 in a cross configuration, located below the hole 4a, opening onto the exterior face of the pad 5 and possibly communicating with the bottom of the hole 4a.

According to FIG. 2, the collar 6 extends toward the foot 3c of the central element 3 in the form of a skirt 6a capping the part 4b of the peripheral element 4 away from the neck 7.

Moreover, still according to FIG. 2, a string 12 attached to the peripheral element 4 allows the disposable device 1 to be extracted from the body cavity 2 after it has treated the latter, that is to say after the substrate of the central element 3 has liquefied.

According to FIG. 3, a closed temporary protective case 10 encases the central element 3 and peripheral element 4 when these elements are assembled, as described earlier. This casing consists, for example, of a substrate with the properties described above, for example based on gelatin. What this means is that the casing is made of a material which is relatively solid at ambient temperature and outside the body cavity so that within this cavity and at the body temperature, this material melts and thus constitutes another part of the liquid phase of the active liquid previously defined. However, this casing 10 may consist of a hard and solid excipient, for example sucrose, as used in a galenic form to obtain sugar-coated pills, and capable of dissolving or breaking up in contact with any bodily liquid present in the cavity 2.

According to FIG. 4, the central element 3 is a capsule, the wall 8 of which consists of the previously defined substrate and the interior of which contains another liquid 15, active or otherwise, the wall 8 being closed and sealed at ambient temperature and outside the body. The liquid thus contained in the capsule makes it possible to increase the amount of liquid phase of the active liquid. This liquid 15 may have any appropriate form, for example oily, and may contain all or part of a treatment agent as previously described, in solution or in suspension in said liquid.

As is not depicted according to another embodiment of the invention, the casing 10 depicted in FIG. 4 may be omitted, while the wall 8 forms an appendage that can be broken off at its opposite end of the pad 5, which allows the user to open the capsule just before inserting the device into the body cavity and to benefit from a small amount of the liquid 15 to moisten the exterior of said device at the time of inserting it into said cavity.

According to FIGS. 1 to 4, a device according to the invention, prior to its insertion into the body cavity 2, comprises a distal part 1a, via which it is inserted into the body cavity 2, and a proximal part 1b, the largest transverse diameter of which is smaller than the largest transverse diameter of the distal part 1a. This allows the device to be held temporarily in the cavity before the active liquid takes over by swelling the pad 5.

This configuration also makes it possible to limit or eliminate any contact between the mucous membrane of the body cavity 2 and the absorbent material when the pad 5 is in the dry state at the time of insertion of the device 1; as such contact could not only give rise to a not insignificant amount of friction but may also be a source of discomfort or pain to the user. On the other band, by virtue of the configuration adopted, it is only the distal part 1a, covered with the relatively slippery collar 7, which slides in contact with the mucous membrane of the body cavity as the device is being inserted.

A disposable device as previously described affords the following essential advantages:

the absorption of the treatment agent or agents by the mucous membrane of the body cavity is more complete and rapid;

the incorporation of this treatment agent into the substrate of the central element makes it possible to have a precise and uniform amount of treatment agent which is also protected by the substrate, this keeping it away from any oxidation or hydrolysis, for example;

the mucous membrane of the cavity and the active liquid are brought fully into contact with each other.

What is claimed is:

1. A disposable device, for transferring and/or circulating an active liquid into a body cavity, having sufficient intrinsic consistency to allow it to be inserted into said cavity by pushing, said device comprising:

a central element comprising a substrate that is relatively solid at ambient temperature, outside the body cavity, and that becomes relatively liquid inside the body cavity so that within this cavity said central element liquefies at least partially to generate at least part of a liquid phase of the active liquid;

a peripheral element, having a distal end and a proximal end, arranged around the central element, and radially surrounding at least part of the central element, comprising a pad designed to collect and absorb active liquid dispensed into the body cavity by expanding and thus coming to press in a sealed manner against mucous membrane of the body cavity; and a temporary protective casing covering at least said distal end of said central element and said peripheral element, comprising a substance that is relatively solid at ambient temperature, outside the body cavity, and that becomes relatively liquid inside the body cavity.

2. Device according to claim 1, wherein an agent for treating the body cavity is distributed in a solid substrate of the central element.

3. Device according to claim 2, wherein the active liquid comprises a treatment agent selected from the group consisting of wetting agents, agents for solubilizing and fluidizing a bodily fluid or liquid present in the body cavity, therapeutic agents, prophylactic agents, diagnostic agents, cosmetic agents, personal hygiene agents, antiseptics, bactericides, fungicides and spermicides.

4. Device according to claim 1, wherein the peripheral element has a hole, the shape and size of said hole being tailored to receive a body of the central element.

5. Device according to claim 1, wherein the central element has a foot with a bulging shape, while the peripheral element has a flared part, the shape and size of said flared part being tailored to retain the foot of the central element.

6. Device according to claim 1, wherein the central element is a capsule, a wall of said capsule being comprised of said substrate, and the interior of said capsule containing another liquid, said wall being closed and sealed with respect to said another liquid, at ambient temperature and outside the body cavity.

7. Device according to claim 1, wherein said device comprises a temporary protective casing encasing the central element and the peripheral element when these elements are assembled.

8. Device according to claim 1, wherein said substrate comprises gelatin.

9. Device according to claim 4, wherein the pad is bored with at least one radial passage opening onto an exterior face of said pad, and communicating with said hole.

10. A device for transferring a liquid into a body cavity, comprising:
   an expandable element that is expandable upon absorption of liquid, said expandable element having a distal end and a proximal end;
   a source of liquid partially radially surrounded by said expandable element; and
   a material at least partially covering said distal end of said expandable element and said source of liquid, said material comprising a substance that is relatively solid in ambient temperature and atmosphere, but that can at least partially enter a liquid state when in a body cavity.

11. A device according to claim 10, wherein said source of liquid extends distally beyond a distal end of said expandable element.

12. A device according to claim 10, wherein said material at least partially melts and/or dissolves under conditions in said body cavity.

13. A device according to claim 10, wherein said material is not present at said proximal end.

14. A device according to claim 13, wherein said material forms a collar around a distal body portion of said distal end of said expandable element.

15. A device according to claim 10, wherein said source of liquid comprises a wall that is closed and sealed while said device is outside said body cavity, and said wall encloses a substance that is liquid in ambient temperature.

16. A device according to claim 15, wherein said wall comprises a substance that is relatively solid in ambient temperature and atmosphere, but that can at least partially enter a liquid state when in a body cavity.

17. A device according to claim 10, wherein said source of liquid extends from within a proximal half of said expandable element through a distal half of said expandable element.

18. A device according to claim 10, wherein said expandable element comprises a foam of a biocompatible plastic material.

19. A device according to claim 10, wherein said liquid comprises a local treatment agent.

20. A device according to claim 10, wherein said liquid comprises a systemic treatment agent.

21. A device according to claim 10, wherein said liquid comprises at least one member selected from the group consisting of antiseptics, bactericides, spermicides and fungicides.

22. A device for transferring a liquid into a body cavity, comprising:
   an expandable element that is expandable upon absorption of liquid, said expandable element having a distal end and a proximal end;
   a source of liquid at least partially radially surrounded by said expandable element, said source of liquid comprising a wall that is closed and sealed while said device is outside said body cavity, and said wall encloses a substance that is liquid in ambient temperature; and
   a material at least partially covering said distal end of said expandable element and said source of liquid, said material comprising a substance that is relatively solid in ambient temperature and atmosphere, but that can at least partially enter a liquid state when in a body cavity.

23. A device according to claim 22, wherein said source of liquid extends distally beyond a distal end of said expandable element.

24. A device according to claim 22, wherein said material at least partially melts and/or dissolves under conditions in said body cavity.

25. A device according to claim 22, wherein said material is not present at said proximal end.

26. A device according to claim 25, wherein said material forms a collar around a distal body portion of said distal end of said expandable element.

27. A device according to claim 22, wherein said wall comprises a substance that is relatively solid in ambient temperature and atmosphere, but that can at least partially enter a liquid state when in a body cavity.

28. A device according to claim 22, wherein said source of liquid extends from within a proximal half of said expandable element through a distal half of said expandable element.

29. A device according to claim 22, wherein said expandable element comprises a foam of a biocompatible plastic material.

30. A device according to claim 22, wherein said liquid comprises a local treatment agent.

31. A device according to claim 22, wherein said liquid comprises a systemic treatment agent.

32. A device according to claim 22, wherein said liquid comprises at least one member selected from the group consisting of antiseptics, bactericides, spermicides and fungicides.

33. A device for transferring a liquid into a body cavity, comprising:
   an expandable element that is expandable upon absorption of liquid, said expandable element having a distal end and a proximal end;
   a source of liquid at least partially radially surrounded by said expandable element and extending from within a proximal half of said expandable element through a distal half of said expandable element; and
   a material at least partially covering said distal end of said expandable element, said material comprising a substance that is relatively solid in ambient temperature and atmosphere, but that can at least partially enter a liquid state when in a body cavity.

34. A device according to claim 33, wherein said source of liquid extends distally beyond a distal end of said expandable element.

35. A device according to claim 33, wherein said material at least partially melts and/or dissolves under conditions in said body cavity.

36. A device according to claim 33, wherein said material is not present at said proximal end.

37. A device according to claim 36, wherein said material forms a collar around a distal body portion of said distal end of said expandable element.

38. A device according to claim 33, wherein said source of liquid comprises a wall that is closed and sealed while said device is outside said body cavity, and said wall encloses a substance that is liquid in ambient temperature.

39. A device according to claim 38, wherein said wall comprises a substance that is relatively solid in ambient temperature and atmosphere, but that can at least partially enter a liquid state when in a body cavity.

40. A device according to claim 33, wherein said source of liquid comprises a body that is relatively solid in ambient temperature and atmosphere.

41. A device according to claim 33, wherein said expandable element comprises a foam of a biocompatible plastic material.

42. A device according to claim 33, wherein said liquid comprises a local treatment agent.

43. A device according to claim 33, wherein said liquid comprises a systemic treatment agent.

44. A device according to claim 33, wherein said liquid comprises at least one member selected from the group consisting of antiseptics, bactericides, spermicides and fungicides.

45. A device for transferring a liquid into a body cavity, comprising:
   an expandable element that is expandable upon absorption of liquid; and
   a source of liquid at least partially radially surrounded by said expandable element and comprising a central element extending from within a proximal half of said expandable element through a distal half of said expandable element;
   wherein central said element comprises a substance that is relatively solid in ambient temperature and atmosphere, but that can at least partially enter a liquid state when in a body cavity; and
   a temporary protective casing covering at least said distal end of said central element and said peripheral element, comprising a substance that is relatively solid at ambient temperature, outside the body cavity, and that becomes relatively liquid inside the body cavity.

46. A device according to claim 45, wherein said central element extends distally beyond a distal end of said expandable element.

47. A device according to claim 45, wherein said substance at least partially melts and/or dissolves under conditions in said body cavity.

48. A device according to claim 45, wherein said expandable element has a distal end and a proximal end, and further comprising a material at least partially covering said distal end of said expandable element, said material comprising a substance that is relatively solid in ambient temperature and atmosphere, but that can at least partially enter a liquid state when in a body cavity.

49. A device according to claim 48, wherein said material covers an exposed portion of said central element.

50. A device according to claim 45, wherein said central element comprises a wall of said substance that is closed and sealed while said device is outside said body cavity, and said wall encloses a liquid in ambient temperature.

51. A device according to claim 45, wherein said central element comprises a body that is relatively solid in ambient temperature and atmosphere.

52. A device according to claim 45, wherein said liquid comprises a local treatment agent.

53. A device according to claim 45, wherein said liquid comprises a systemic treatment agent.

54. A device according to claim 45, wherein said liquid comprises at least one member selected from the group consisting of antiseptics, bactericides, spermicides and fungicides.

55. A device for transferring a liquid into a body cavity, comprising:
   an expandable element that is expandable upon absorption of liquid and comprises a foam of a biocompatible plastic material, said expandable element having a distal end and a proximal end;
   a source of liquid partially radially surrounded by said expandable element and comprising a central element extending from within a proximal half of said expandable element through a distal half of said expandable element and distally beyond a distal end of said expandable element, said central element comprising a wall that is closed and sealed while said device is outside said body cavity;
   said wall comprising a substance that is relatively solid in ambient temperature and atmosphere, but that can at least partially enter a liquid state when in a body cavity, and enclosing a substance that is liquid in ambient temperature; and
   a material at least partially covering said distal end of said expandable element, said material comprising a substance that is relatively solid in ambient temperature and atmosphere, but that can at least partially enter a liquid state when in a body cavity.

56. A device according to claim 55, wherein said material covers an exposed portion of said central element.

57. A device according to claim 55, wherein said material forms a collar around a distal body portion of said distal end of said expandable element.

58. A device according to claim 55, wherein said liquid comprises a local treatment agent.

59. A device according to claim 55, wherein said liquid comprises a systemic treatment agent.

60. A device according to claim 55, wherein said liquid comprises at least one member selected from the group consisting of antiseptics, bactericides, spermicides and fungicides.

61. A method of transferring a liquid into a vagina, comprising inserting a device according to claim 1 into and in contact with walls of said vagina, allowing said liquid to be released from said source of liquid in said vagina, and withdrawing said device from said vagina.

62. A method according to claim 61, wherein a proximal end of said expandable element expands to press in a sealed manner against said walls of said vagina upon absorbing said liquid, to seal against external flow of the liquid from the vagina.

63. A method of transferring a liquid into a vagina, comprising inserting a device according to claim 10 into and in contact with walls of said vagina, allowing said liquid to be released from said source of liquid in said vagina, and withdrawing said device from said vagina.

64. A method according to claim 63, wherein said proximal end of said expandable element expands to press in a sealed manner against said walls of said vagina upon absorbing said liquid, to seal against external flow of the liquid from the vagina.

65. A method of transferring a liquid into a vagina, comprising inserting a device according to claim 22 into and in contact with walls of said vagina, allowing said liquid to be released from said source of liquid in said vagina, and withdrawing said device from said vagina.

66. A method according to claim 65, wherein said proximal end of said expandable element expands to press in a sealed manner against said walls of said vagina upon absorbing said liquid, to seal against external flow of the liquid from the vagina.

67. A method of transferring a liquid into a vagina, comprising inserting a device according to claim 33 into and in contact with walls of said vagina, allowing said liquid to be released from said source of liquid in said vagina, and withdrawing said device from said vagina.

68. A method according to claim 67, wherein said proximal end of said expandable element expands to press in a sealed manner against said walls of said vagina upon absorbing said liquid, to seal against external flow of the liquid from the vagina.

69. A method of transferring a liquid into a vagina, comprising inserting a device according to claim 45 into and in contact with walls of said vagina, allowing said liquid to be released from said source of liquid in said vagina, and withdrawing said device from said vagina.

70. A method according to claim 69, wherein a proximal end of said expandable element expands to press in a sealed manner against said walls of said vagina upon absorbing said liquid, to seal against external flow of the liquid from the vagina.

71. A method of transferring a liquid into a vagina, comprising inserting a device according to claim 55 into and in contact with walls of said vagina, allowing said liquid to be released from said source of liquid in said vagina, and withdrawing said device from said vagina.

72. A method according to claim 71, wherein said proximal end of said expandable element expands to press in a sealed manner against said walls of said vagina upon absorbing said liquid, to seal against external flow of the liquid from the vagina.

* * * * *